United States Patent [19]
Fairand et al.

[11] 4,246,793
[45] Jan. 27, 1981

[54] NONDESTRUCTIVE TESTING

[75] Inventors: Barry P. Fairand, Upper Arlington; Matthew J. Golis, Columbus, both of Ohio

[73] Assignee: Battelle Development Corporation, Columbus, Ohio

[21] Appl. No.: 10,387

[22] Filed: Feb. 8, 1979

Related U.S. Application Data

[63] Continuation-in-part of Ser. No. 859,808, Dec. 12, 1977, abandoned.

[51] Int. Cl.$^3$ ............................................. G01N 29/04
[52] U.S. Cl. ........................................ 73/628; 73/643
[58] Field of Search ................................. 73/643, 628

[56] References Cited

U.S. PATENT DOCUMENTS 3,978,713  9/1976  Penney .................................. 73/643

OTHER PUBLICATIONS

"Ultrasonic Testing of Materials" 2d Ed. by Krautkramer, Springer-Verlag, NY, NY, Translation of German 1975, pp. 150–162.
"Conversion of Electromagnetic to Acoustic Energy by Surface Heating" by Gournay, from The Journal of the Acoustical Society, 1966, pp. 1322–1330.
"Laser Generated Ultrasonic Beams" by Felix from Rev. of Scientific Instr. pp. 1106–1108 (1974).
"Optical Excitation of Sound Waves", Bunkin et al., Soviet Phys. Acoust. 19 (3) pp. 203–211 (1973).

Primary Examiner—James J. Gill
Attorney, Agent, or Firm—Philip M. Dunson; Thomas W. Winland; Barry S. Bissell

[57] ABSTRACT

Methods (and apparatus) for nondestructively testing a body of material having a surface in contact with a gaseous environment (e.g. air, nitrogen, or inert gas), that comprise (A) the step of (and means for) directing to a region at the surface of the body a pulse of laser radiation having sufficient energy density and sufficiently long wavelength to initiate in the adjacent gas a blast wave that impinges on the surface and provides an ultrasonic wave in the body, and (B) the further step of (and means for) detecting a portion of the ultrasonic wave that has been affected by the body. The radiation directing means typically comprises a laser that provides a pulse having a duration of about 0.01 to 10 microseconds, and means for focusing the pulse to provide an energy density of at least about 5 Joules per square centimeter. The detecting means typically comprises an electromagnetic or capacitive transducer.

19 Claims, 8 Drawing Figures

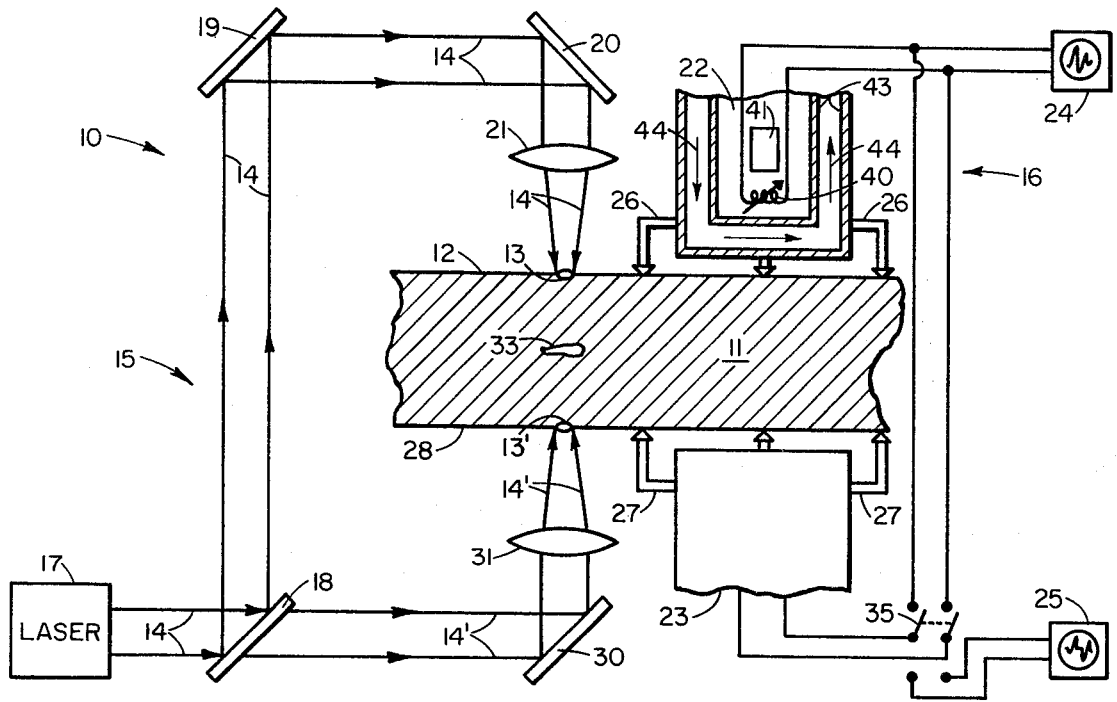
FIG. 1
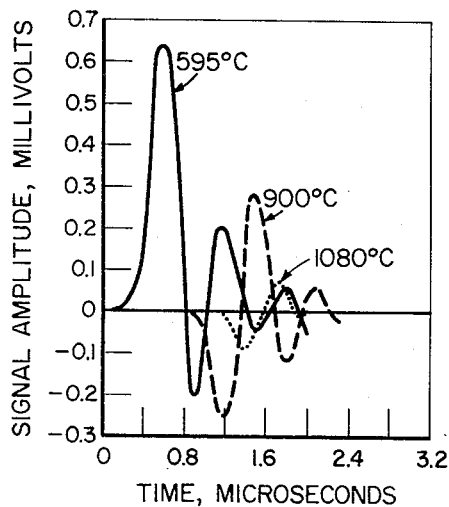
FIG. 2
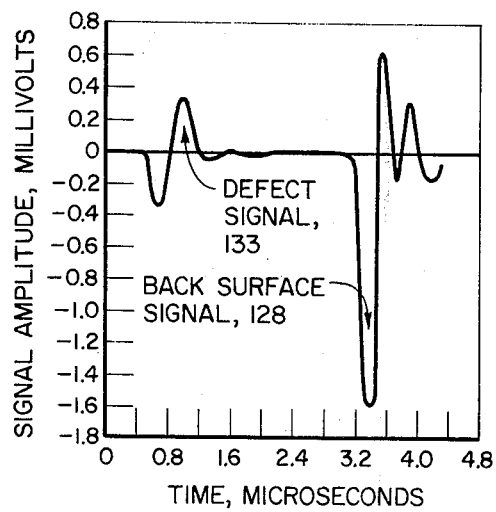
FIG. 3
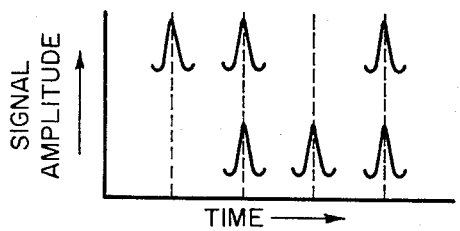
FIG. 4  $\dfrac{2x}{V_s}$  $\dfrac{D}{V_s}$  $\dfrac{2(D-x)}{V_s}$  $\dfrac{2D}{V_s}$

4,246,793

NONDESTRUCTIVE TESTING

PRIOR APPLICATION

This is a continuation in part of U.S. Patent Application Ser. No. 859,808, filed Dec. 12, 1977, and now abandoned.

BACKGROUND

The present invention relates to non-contact methods and apparatus for nondestructively investigating the internal properties and defect structures of materials. The technique typically uses a pulsed laser to generate a pressure pulse at the surface of the material being interrogated and a non-contact receiver such as an electromagnetic pickup coil or other transducer to detect the scattered or reflected signal. The method is especially useful for nondestructively evaluating the properties of materials that are at elevated temperatures.

The amplitude of the pressure pulse that is generated at the material surface is maintained below the material's elastic limit in order to avoid permanent changes in the material's properties yet is of sufficient amplitude for the scattered or reflected signal to be detected by a low efficiency non-contact device.

The pressure pulse probes the internal structure of materials in a manner similar to conventional ultrasonic non-destructive testing. The intensity of the laster induced source of ultrasound, however, can be made at least a factor of 10 more intense than standard sources of ultrasound. This permits a low efficiency non-contact detector such as an electromagnetic coil to be used to detect the scattered or reflected signal without stringent requirements on signal amplification or elaborate processing schemes to distinguish the signal from background noise. Furthermore, a pulsed laser generates a short discrete pulse of ultrasound. This allows precise time discrimination schemes to be used in processing of signals, particularly in pulse-echo techniques.

Past techniques for generation of ultrasound have included dielectric breakdown in liquids, generation of thermo-elastic waves at unconfined surfaces wherein a surface layer of material is rapidly and nonuniformly heated to temperatures below its vaporization point, and vaporization of a small amount of surface material by the impinging laser beam. Transparent materials placed directly on the surface of the absorbent material also have provided an effective method of enhancing the amplitude of the signal that is generated at an unconfined surface.

The present method of generating an ultrasonic signal does not rely on the use of a transparent overlay (which in many cases of nondestructive evaluation, e.g., high temperature materials, would not be practical) to generate an intense source of ultrasound. Also the present technique does not disturb the surface of the material being evaluated, which occurs when the surface is vaporized by the incident laser beam. The present method involves initiation of a blast wave in the atmospheric environment in the vicinity of the surface of the material being evaluated. Pulsed carbon dioxide and neodymium-glass lasers are effective systems for generating intense ultrasonic signals by this method. Other pulsed lasers with wavelengths intermediate to these two systems such as carbon monoxide lasers also provide attractive systems for generating intense pulses of ultrasonic energy in materials. A significant fraction of such signals generated by systems of these types contain low frequency components which can propagate through large thicknesses of material. This is an important consideration when large parts are being evaluated.

A major problem encountered in the steel industry is the inability to nondestructively interrogate hot steel billets to detect internal defect structures before cooling. The present technique can detect defect structures in hot steel.

SUMMARY

A typical method according to the present invention, for nondestructively testing a body of material having a surface in contact with a gaseous environment, comprises directing to a region at the surface of the body a pulse of laser radiation having sufficient energy density and sufficiently long wavelength to initiate in the adjacent gas a blast wave that impinges on the surface and provides an ultrasonic wave in the body, and detecting a portion of the ultrasonic wave that has been affected by the body.

The energy density of the radiation typically is at least about 5 to 10 Joules per square centimeter with a wavelength of about 10.6 micrometers; at least about 50 to 100 Joules per square centimeter with a wavelength of about 1.06 micrometers; and at least about an energy density interpolated or extrapolated from the foregoing energy densities with another wavelength, with the energy density approximately inversely proportional to the wavelength. The surface region area typically is at least about 0.1 square millimeter.

The gas typically comprises essentially air, nitrogen, or an inert gas, and the region typically has an area of about 0.1 to 10 square centimeters. Typically the wavelength of the radiation is about 1 to 15 micrometers, the duration of the pulse is about 0.01 to 10 microseconds, and the fundamental frequency of the ultrasonic wave is about 0.1 to 20 megahertz. The detecting typically includes providing a visible record indicative of the location of a surface or other discontinuity in the body.

Typical apparatus according to the present invention, for nondestructively testing a body of material having a surface in contact with a gaseous environment, comprises means for directing to a region at the surface of the body a pulse of laser radiation having sufficient energy density and sufficiently long wavelength to initiate in the adjacent gas a blast wave that impinges on the surface and provides an ultrasonic wave in the body, and means for detecting a portion of the ultrasonic wave that has been affected by the body.

The radiation directing means typically comprises a carbon dioxide or neodymium-glass laser that provides a pulse having a duration of about 0.01 to 10 microseconds, and means for focusing the pulse to provide an energy density of at least about 5 to 10 Joules per square centimeter for the carbon dioxide laser and at least about 50 to 100 Joules per square centimeter for the neodymium-glass laser in a region having an area of about 0.1 to 10 square centimeters, and thus to provide in the body an ultrasonic wave having a fundamental frequency of about 0.1 to 20 megahertz.

The detecting means typically comprises means responsive to the ultrasonic wave for varying the current in an electrical circuit and means for recording the resulting variations. Typically a surface of the body is electrically conductive and the detecting means comprises an electromagnetic transducer or a capacitive transducer located adjacent to the conductive surface and spaced therefrom. Where the detecting means comprises an electromagnetic transducer, it typically is resonant at substantially the fundamental frequency of the ultrasonic wave. The resonant frequency of the transducer may be adjustable. The apparatus may comprise also means for maintaining the transducer in a position adjacent to a surface of the body and at a substantially constant average spacing therefrom during the testing.

The radiation directing means may provide a pulse to each of a plurality of regions at the surface of the body, and then the detecting means typically comprises a plurality of transducers and means for maintaining each transducer in a different location adjacent to, and spaced from, a surface of the body.

DRAWINGS

FIG. 1 is a schematic front view, partially in section, illustrating typical embodiments of the present invention.

FIG. 2 is a graphical reproduction of the oscilloscope traces obtained in a typical test according to the invention.

FIG. 3 is a reproduction as in FIG. 2 for another typical test.

FIG. 4 is a similar reproduction for another typical test.

PREFERRED EMBODIMENTS

Figure 5:
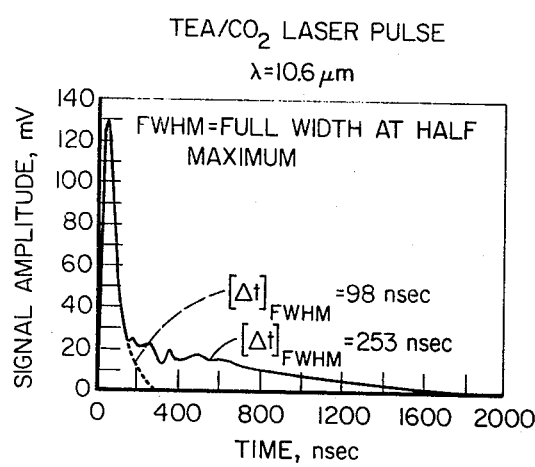
FIG. 5 is a graphical reproduction of the oscilloscope trace showing the shapes of two typical laser pulses used in some experiments described herein.

Typical apparatus 10, according to the present invention, for nondestructively testing of body material 11 having a surface 12 in contact with a gaseous environment, comprises means 15 for directing to a region 13 at the surface 12 of the body 11 a pulse of laser radiation 14 having sufficient energy density and sufficiently long wavelength to initiate in the adjacent gas a blast wave that impinges on the surface 12 and provides an ultrasonic wave in the body 11, and means 16 for detecting a portion of the ultrasonic wave that has been affected by the body 11.

The radiation directing means 15 typically comprises a carbon dioxide or neodymium-glass laser 17 that provides a pulse 14 having a duration of about 0.01 to 10 microseconds, (as via a beam splitter 18 and mirrors 19, 20), and means, such as a lens 21, for focusing the pulse 14 to provide an energy density typically of at least 5 to 10 Joules per square centimeter with a carbon dioxide laser, and typically at least about 50 to 100 with a neodymium-glass laser, in a region 13 having an area of at least about 0.1 square millimeter and typically about 0.1 to 10 square centimeters, and thus to provide in the body 11 an ultrasonic wave having a fundamental frequency of about 0.1 to 20 megahertz.

The detecting means 16 typically comprises means 22 or 23 responsive to the ultrasonic wave for varying the current in an electrical circuit 16 and means such as an oscilloscope 24 or 25 for recording the resulting variations. Typically the surface 12 or 28 is electrically conductive and the detecting means 16 comprises an electromagnetic transducer 22 or a capacitive transducer 23 located adjacent to the conductive surface 12 or 28 and spaced therefrom. Where the detecting means 16 comprises an electromagnetic transducer 22, it typically is resonant at substantially the fundamental frequency of the ultrasonic wave. The resonant frequency of the transducer 22 may be adjustable, as by varying the size of the coil 40 or the number of turns in it. The apparatus 10 may comprise also means 26 or 27 for maintaining the transducer 22 or 23 in a position adjacent to a surface of the body 11 at a substantially constant average spacing therefrom during the testing.

The radiation directing means 15 may also provide a pulse 14' (as via the beam splitter 18, a mirror 30, and a lens 31) to another region 13' at a surface 28 of the body 11, and then the detecting means 16 typically comprises a plurality of transducers 22, 23 and means 26, 27 for maintaining each transducer 22, 23 in a different location adjacent to, and spaced from, a surface 12, 28 of the body 11. For optimum operation where both transducers 22, 23 are used, they should both be of the same type, preferably electromagnetic, and have substantially identical response characteristics. Additional pulses may also be provided, with an additional transducer for each additional pulse.

A typical method according to the present invention, for nondestructively testing a body of material 11 having a surface 12 in contact with a gaseous environment, comprises directing to a region 13 at the surface 12 of the body 11 a pulse of laser radiation 14 having sufficient energy density and sufficiently long wavelength to initiate in the adjacent gas a blast wave that impinges on the surface 12 and provides an ultrasonic wave in the body 11, and detecting a portion of the ultrasonic wave that has been affected by the body 11.

The energy density of the radiation 14 typically is at least about 5 to 10 Joules per square centimeter with a wavelength of about 10.6 micrometers; at least about 50 to 100 Joules per square centimeter with a wavelength of about 1.06 micrometers; and at least about an energy density interpolated or extrapolated from the foregoing energy densities with another wavelength, with the energy density approximately inversely proportional to the wavelength. The surface region area 13 typically is at least about 0.1 square millimeter.

The gas typically comprises essentially air, nitrogen or an inert gas, and the region 13 typically has an area of about 0.1 to 10 square centimeters. Typically the wavelength of the radiation 14 is about 1 to 15 micrometers, the duration of the pulse 14 is about 0.01 to 10 microseconds, and the fundamental frequency of the ultrasonic wave is about 0.1 to 20 megahertz.

The detecting typically includes providing a visible record, as at 24 or 25, indicative of the location of a surface 12 or 28 or other discontinuity (as at 33) in the body 11.

Initiation of a blast wave in the gas environment adjacent to the material surface is caused by a source of priming electrons. Below the laser power density threshold for initiation of a blast wave most of the laser radiation incident on the surface is reflected. When the threshold power density is reached, the intensity of the electric field associated with the laser light radiation is sufficient strong in the vicinity of the material surface to generate free electrons in the gas or at the material surface due to field emission. The electric fields are enhanced near the target surface because of constructive interference between the incident and reflected electromagnetic waves. Surface defect enhanced fields are expected to lower the laser power density threshold for production of free electrons compared to a theoretically perfect surface.

In the cases where the material to be tested is at elevated temperature, e.g., hot steel billets, thermionic emission may provide another important source of priming electrons.

The free electrons produced in the vicinity of the material surface are strong absorbers of the incident laser radiation. The gas adjacent to the surface is heated with emission of additional electrons. The process rapidly cascades with the generation of a blast wave in the gas.

EXAMPLES

A $CO_2$ laser 17 with an effective or equivalent pulse width of approximately 0.25 microsecond was used to generate ultrasonic signals in hot steel blocks 11 and a noncontact electromagnetic transducer 22 was used to detect these signals.

The first experiments were designed to demonstrate that laser induced ultrasonic signals can be propagated and detected through thick steel specimens at temperatures ranging from the standard room value to a value in excess of the austenizing temperature where nondestructive evaluation of steel is desired. The 4.5 cm thick cold rolled steel block 11 was heated and then manually removed to a stand where the laser beam 14' was directed to one surface 28 of the steel block 11, which was in an air environment at normal room conditions. An electromagnetic transducer 22 with a 32 turn copper coil 40 and a permanent magnet 41, providing a static magnetic field of 1.53 kilogauss, was placed near the opposite surface 12 to detect the transmitted ultrasonic signal. A one meter focal length germanium lens 31 was used to focus the laser beam 14' down to various spot sizes at the region 13' at the metal surface 28. No detectable signals were observed until the incident laser power density exceeded about $2 \times 10^7$ W/cm$^2$. The laser beam 14' was subsequently focused down to a spot size at the region 13' of approximately 0.24 cm$^2$ (about 0.6 cm diameter) which resulted in a laser energy density at the metal surface 28 of about 40 J/cm$^2$ ($1.6 \times 10^8$ W/cm$^2$).

The temperature of the steel block 11 was monitored with a chromel-alumel thermocouple which was peened into the surface of the steel block 11. Output of the electromagnetic transducer 22 was displayed on an oscilloscope 24.

Graphical reproductions of the oscilloscope traces are shown in FIG. 2. The 595 C curve is a composite signal made up of a Lorentz component and a magnetostrictive component, where the latter component is due to the ferromagnetic character of the steel block. The two higher temperature results are both above the Curie temperature where the test specimen is paramagnetic and the magnetostrictive portion of the signal disappears. The reduction in the amplitude of the signal at 1080 C is the result of an austenitic phase transformation which results in grain growth within the specimen and increased attenuation of the signal. The displacement in time of the three signals is caused by the lower longitudinal sound velocity in the hotter material.

A set of experiments were performed to demonstrate that a defect can be detected in a hot steel block. The temperature was 787 C. The laser beam 14 was directed to the same surface 12 where the electromagnetic transducer 22 was located in order to utilize a pulse echo technique to detect the signal reflected from the back surface 28 and the defect 33. The germanium lens 21 was adjusted to give a laser energy density of approximately 45 J/cm$^2$ ($1.8 \times 10^8$ W/cm$^2$) at the region 13 at the steel surface 12.

An example of the signal detected by the transducer 22 and displayed on an oscilloscope 24 is shown in FIG. 3. The difference in time between the defect signal 133 and the back surface signal 128 is due to the difference in propagation distance of the two signals.

In all of the experiments, the energy density was about 1–100 J/cm$^2$ (about $4 \times 10^6$–$4 \times 10^8$ W/cm$^2$) and the duration of the laser pulse was about 0.1–10 microseconds.

The electromagnetic transducer 25 typically consists of a pickup coil 40 and a permanent magnet 41. An electromagnetic coil also can be used instead of the permanent magnet 41. The transducer 22 operates on the basis of the Lorentz Force wherein motion of an electrical conductor (the surface 12 of the body 11) in the presence of a magnetic field will induce a current in an adjacent pickup coil 40. If the conductor is ferromagnetic an additional current component is introduced due to magnetostrictive forces.

A typical electromagnetic transducer 22 consists of a copper pickup coil 40 and a rare earth permanent magnet 41, i.e., Co/Sm. The size of such a device is a few inches on a side.

Random motion or vibration of the part 11 being interrogated can be a problem if the distance between the pickup coil 40 and the material 11 is not about a constant during the time the part 11 is being interrogated. This is true because the efficiency of the transducer 22 is a function of the standoff distance from the surface 12. To avoid this problem, the transducer 22 typically is contained in a jacket 43 through which a coolant liquid 44 circulates, and this assembly is momentarily brought into proximity with the part 11 being interrogated, with the average space between the transducer 22 and the adjacent surface 12 maintained substantially constant by a three-point contact device 26 or other appropriate spacing control, such as a servo mechanism.

Time discrimination schemes are easily incorporated into the present method of detecting defects in high temperature materials. For example, consider the case where the laser beam is split into two components 14, 14' and these components are directed to the two opposite surfaces 12, 28 of the part being interrogated as shown in FIG. 1. The transducers 22, 23 will each see three signals, one due to scatter off the defect 33; one due to reflection off the opposite surface 28 or 12; and one due to the source of sound transmitted from the other surface. If $V_s$ is the speed of sound in the material being interrogated, D is the thickness of the body 11, and x is the distance from the surface 12 to the defect 33, one transducer will see signals at times $$\frac{2x}{V_s}, \frac{D}{V_s}, \frac{2D}{V_s}$$

and the other will see signals at $$\frac{2(D-x)}{V_s}, \frac{D}{V_s}, \frac{2D}{V_s}$$

$D/V_s$ is the transmitted signal,
$2D/V_s$ is reflection off the opposite surface, and $$\frac{2x}{V_s} \text{ and } \frac{2(D-x)}{V_s}$$

are signals due to scattering off the defect.

Consider a specific example where $x=D/4$. When the signals from both transducers 22 and 23 are displayed on a dual beam scope 24 (with the switch 35 in its upper position), they appear in time according to FIG. 4. The presence of a defect can be found by looking for time correlated signals arriving in the time interval $0-2D/V_s$.

Several experiments were conducted later concerning effects of laser power density and energy density in generating ultrasonic waves.

The mechanism for generating the ultrasonic signal is based on initiation of a blast wave in the gaseous environment that is adjacent to the body.

The threshold laser conditions for generation of this blast wave vary with laser wavelength and duration of the laser pulse. A test of the threshold conditions at long wavelengths and long laser pulses was made with a TEA-$CO_2$ laser. A test of the threshold conditions at short wavelengths and short laser pulses were made with a "Q" switched neodymium-glass laser.

The TEA-$CO_2$ laser emits radiation at 10.6 micrometers. The laser pulse measured with a photon drag detector is shown by the solid curve in FIG. 5. Graphical integration of this pulse gives an effective or equivalent laser pulse whose full width at one-half peak power is 253 nanoseconds.

Figure 6:
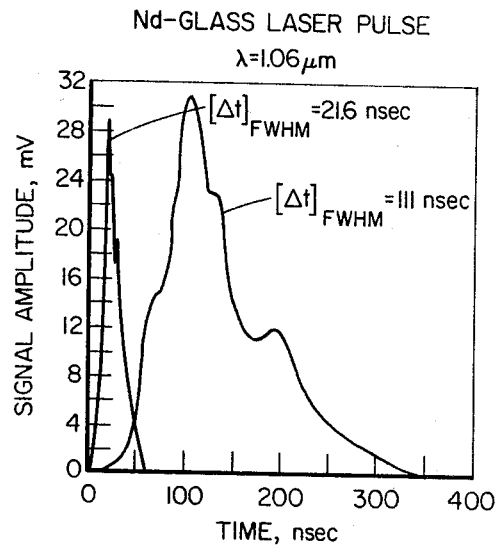
FIG. 6 is a reproduction as in FIG. 5 for two other such laser pulses used in other such experiments.

The Nd-glass laser emits radiation at 1.06 micrometers. The laser pulse measured with a photodiode detector is shown by the thin curve on the left in FIG. 6. Graphical integration of this pulse gives an effective or equivalent laser pulse whose full width at one-half peak power is 21.6 nanoseconds.

The steel specimen 11 and the electromagnetic detector 22 described above were used in the experiments. The same experimental setup was used (as in FIG. 1) where the electromagnetic detector 22 was placed on the same surface 12 as was impinged by the laser beam 14.

Signals reflected off the back surface 28 and a side drilled hole (not shown) and detected by the electromagnetic pickup 22 were measured as a function of the incident laser light intensity at the region 13.

In the case of the TEA-$CO_2$ experiments, the laser spot size at the region 13 was maintained at about 0.34 square centimeters and the intensity was varied by inserting various attenuators (not shown) in the beam 14. Several measurements were made. The amplitude of the signal reflected off the back surface 28 is given in Table I, below, as a function of the incident laser energy density ($J/cm^2$). These numbers are converted to laser power density ($W/cm^2$) by dividing the $J/cm^2$ by the laser pulse width. These numbers also are given in the last five lines in Table I. All measurements were made at about 685 C.

TABLE I

TEA—$CO_2$ SIGNAL MEASUREMENTS AS A FUNCTION OF LASER PARAMETERS. $\lambda = 10.6$ μm

| Laser Energy Density, $J/cm^2$ | Laser Pulse Width, FWHM, nsec | Laser Power Density, $W/cm^2$ | Signal, mv |
|---|---|---|---|
| 8.7 | 98 | $8.9 \times 10^7$ | 0.3 |
| 23 | 98 | $2.3 \times 10^8$ | 1.3 |
| 26 | 253 | $1.0 \times 10^8$ | 1.48 |
| 34 | 253 | $1.3 \times 10^8$ | 2.08 |
| 57 | 253 | $2.3 \times 10^8$ | 2.28 |
| 88 | 253 | $3.5 \times 10^8$ | 3.00 |
| 147 | 253 | $5.8 \times 10^8$ | 3.81 |

Figure 7:
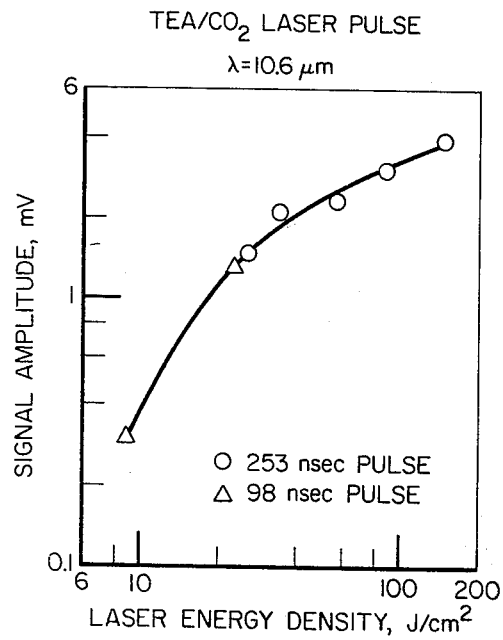
FIG. 7 is a graph of acoustic signal amplitude obtained as a function of laser energy density from some such experiments.

These data are plotted as circles in FIG. 7. The important point to be noted from these data is that the acoustic signals increase significantly with increased energy density, and with increased power density at a given pulse width, over the measured ranges. As is seen from the earlier examples, the acoustic signals also will rapidly fall to approximately a zero value as the laser energy density is decreased. This is because almost all of the 10.6 μm $CO_2$ laser radiation will be reflected from the metal surface when the laser energy density is decreased below the threshold for initiation of a blast wave.

The setup used in the TEA-$CO_2$ experiments also was employed in the Nd-glass experiments. Acoustic signals measured with the laser are given, in the lines where the laser pulse width is 21.6 nsec, in Table II, as a function of the laser parameters. All measurements were made at about 685 C.

Figure 8:
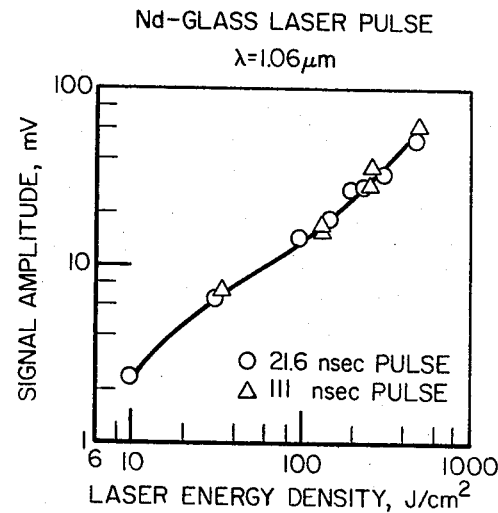
FIG. 8 is a graph as in FIG. 7 from other such experiments.

These data are plotted as circles in FIG. 8.

At the shorter Nd-glass laser wavelength (e.g., 1.06 μm) acoustic signals are generated below the energy density threshold for blast wave initiation.

TABLE II

Nd-GLASS. SIGNAL MEASUREMENTS AS A FUNCTION OF LASER PARAMETERS. $\lambda = 1.06$ μm

| Laser Energy Density, $J/cm^2$ | Laser Pulse Width FWHM, nsec | Laser Power Density, $W/cm^2$ | Signal, mv |
|---|---|---|---|
| 9.7 | 21.6 | $4.5 \times 10^8$ | 2.3 |
| 30.7 | 21.6 | $1.4 \times 10^9$ | 6.4 |
| 33.3 | 111 | $3.0 \times 10^8$ | 7.2 |
| 98.8 | 21.6 | $4.6 \times 10^9$ | 14 |
| 133.2 | 111 | $1.2 \times 10^9$ | 15.6 |
| 133.2 | 111 | $1.2 \times 10^9$ | 17 |
| 145.9 | 21.6 | $6.8 \times 10^9$ | 18 |
| 199.8 | 21.6 | $9.3 \times 10^9$ | 26.9 |
| 230.1 | 21.6 | $1.06 \times 10^{10}$ | 27 |
| 255.3 | 111 | $2.3 \times 10^9$ | 28 |
| 266.4 | 111 | $2.4 \times 10^9$ | 36 |
| 300.8 | 21.6 | $1.4 \times 10^{10}$ | 32.5 |
| 472.7 | 21.6 | $2.19 \times 10^{10}$ | 50.5 |
| 499.5 | 111 | $4.5 \times 10^9$ | 60 |

These signals are due to vaporization of surface material. Signals generated by this mechanism should approach zero as the energy density is further decreased, because surface vaporization will cease.

It is noted in FIG. 8 that there is an increase in signal sensitivity beginning at about 50 $J/cm^2$. (As noted by the increase in slope of the curve). This is due to the onset of a blast wave. Therefore, at the short wavelength, the threshold energy density for initiation of a blast wave is about 50 $J/cm^2$.

In short, the threshold energy density for producing a blast wave varies inversely with the wavelength of the laser radiation.

The amplitude of the signals generated by the Nd-Glass laser could not be compared directly with the signals generated by the TEA-CO₂ laser. This is because the size of the laser spot at the surface of the steel block was different in the two sets of experiments.

In the TEA-CO₂ experiments, the laser spot was maintained at about 0.34 cm², which is equivalent to a spot diameter of 0.66 cm. All of the Nd-Glass experiments except for the highest energy density were conducted at a spot diameter of 1 cm. A spot diameter of 0.8 cm was used in the $2.19 \times 10^{10}$ W/cm² measurement to achieve the high laser energy density (472.7 J/cm²) required for this experiment. The measurement made at $1.4 \times 10^{10}$ W/cm² (300.8 J/cm²) was repeated at this smaller spot size. This information was used to correct the signal amplitude upward by a factor of 2 to account for the effect of spot size so that a direct comparison of amplitude could be made.

The amplitude of the detected signal is a function of the laser spot size because this parameter determines the size of the ultrasonic source. The ultrasonic signal that propagates into the steel is highly directional. Therefore, the amount of ultrasonic energy reflected off a defect or surface and captured by a detector is a function of the diameter of the beam of ultrasound that propagates through the material.

Some experiments conducted still later show that the threshold condition for initiation of a blast wave is defined most conveniently in terms of the laser energy density (J/cm²) incident on the surface of the material being interrogated. This quantity is the product of the laser power density and the effective or equivalent duration of the laser pulse (FWHM). At a laser wavelength of 10.6 μm the laser energy density required to initiate a blast wave is about 5 J/cm². At 1.06 μm it is about 50 J/cm².

The results of the still later experiments conducted at a laser wavelength of 10.6 μm and pulse width of 98 nanoseconds are shown in the first two lines in Table I, and as triangles in FIG. 7. The results of those conducted at 1.06 μm and 111 nanoseconds are shown (in the lines where the laser pulse width is 111 nsec) in Table II, and as triangles in FIG. 8.

The shapes of the curves depicting signal amplitude versus laser energy density are different at 1.06 μm (FIG. 8) and at 10.6 μm (FIG. 7) because the curve at the shorter wavelength is caused by two effects, namely laser induced surface vaporization and initiation of a blast wave. As one proceeds to longer wavelength, surface vaporization will eventually cease (probably at about 3 to 7 μm). This is the case for the 10.6 μm signals. The laser powder density threshold for initiation of vaporization at 1.06 μm and laser pulse widths between 111 nanoseconds and 21.6 nanoseconds ranges from about $10^7$ W/cm² up to about $10^8$ W/cm². The laser energy density equivalent to this range of power densities is about 1 J/cm² up to a few J/cm². On the other hand, the threshold laser energy density for initiation of the blast wave is about 50 J/cm².

The threshold laser energy density required to initiate the blast wave is approximately independent of the size of the laser spot over a wide range of spot sizes. As the spot diameter is made smaller and smaller, a limit should be reached where the laser beam appears as a point source. This diameter has not been determined, but is expected to be in the range of about 0.1 cm. When the laser beam is this diameter or less, its size and the size of the pressure source on the surface of the part being tested probably are significantly different. The pressure source should be larger in diameter than the laser beam because the air plasma that is generated at the blast wave threshold will expand radially as well as normal to the surface.

Selection of test parameters for laser systems other than the TEA-CO₂ laser and neodymium-glass laser depends on the wavelength of the laser system. At the 10.6 μm wavelength of the CO₂ laser the laser energy density needed to initiate a blast wave is about 5 joules per cm² and at the 1.06 μm wavelength of the neodymium-glass laser, this value is about 50 joules per cm². Consider the case where the laser system emits at a wavelength of 3 μm. The hydrogen-fluoride laser is an example of such a system. The laser energy threshold value for initiation of a blast wave is approximately inversely proportional to laser wavelength. Therefore, the threshold energy density for initiation of a blast wave is about 18 joules per cm². If the laser emits 50 joules of energy, the maximum permissible laser spot size at the surface of the part being tested would be 1.9 cm. Spot sizes used under test conditions probably would be somewhat smaller than this value because higher amplitude acoustic signals are generated at smaller spot sizes, e.g., higher laser energy densities. Similar procedures would be used to select parameters for laser systems with other wavelengths.

Operating at energy densities well above the threshold for providing a blast wave is of course desirable, where the available equipment and cost considerations permit, to assure high signal to noise ratios. However, it may be necessary to operate just above the threshold in some circumstances, and this can be done satisfactorily as long as the signals can be distinguished from the noise. Electronic enhancement may be needed in some cases. A few routine preliminary experiments usually are sufficient to select a convenient set of operating parameters.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. A method of nondestructively testing a body of material having a surface in contact with a gaseous environment, that comprises
    directing to a region at the surface of the body a pulse of laser radiation having sufficient energy density and sufficiently long wavelength to initiate in the adjacent gas a blast wave that impinges on the surface and provides an ultrasonic wave in the body, and
    detecting a portion of the ultrasonic wave that has been affected by the body.

2. A method as in claim 1, wherein the energy density of the radiation is at least about 5 Joules per square centimeter with a wavelength of about 10.6 micrometers; at least about 50 Joules per square centimeter with a wavelength of about 1.06 micrometers; and at least about an energy density interpolated or extrapolated from the foregoing energy densities with another wavelength, with the energy density approximately inversely proportional to the wavelength.

3. A method as in claim 2, wherein the surface region area is at least about 0.1 square millimeter.

4. A method as in claim 1, wherein the energy density of the radiation is at least about 10 Joules per square centimeter with a wavelength of about 10.6 micrometers; at least about 100 Joules per square centimeter with a wavelength of about 1.06 micrometers; and at least about an energy density interpolated or extrapolated from the foregoing energy densities with another wavelength, with the energy density approximately inversely proportional to the wavelength.

5. A method as in claim 1, wherein the gas comprises essentially air, nitrogen, or an inert gas.

6. A method as in claim 1, wherein the region has an area of about 0.1 to 10 square centimeters.

7. A method as in claim 1, wherein the wavelength of the radiation is about 1 to 15 micrometers.

8. A method as in claim 1, wherein the duration of the pulse is about 0.01 to 10 microseconds.

9. A method as in claim 1, wherein the fundamental frequency of the ultrasonic wave is about 0.1 to 20 megahertz.

10. A method as in claim 1, wherein the detecting includes providing a visible record indicative of the location of a surface or other discontinuity in the body.

11. A method of nondestructively testing a body of material having an electrically conductive surface in contact with a gaseous environment, that comprises
   directing to a region at the surface of the body a pulse of laser radiation having sufficient energy density and sufficiently long wavelength to initiate in the adjacent gas a blast wave that impinges on the surface and provides an ultrasonic wave in the body, and
   detecting a portion of the ultrasonic wave that has been affected by the body using an electromagnetic transducer that is resonant at substantially the fundamental frequency of the ultrasonic wave and is located adjacent to the conductive surface and spaced therefrom.

12. A method as in claim 11, wherein the resonant frequency of the transducer is adjustable.

13. A method as in claim 11, wherein the transducer is maintained in its position at a substantially constant average spacing from the conductive surface during the testing.

14. A method of nondestructively testing a body of material having a surface in contact with a gaseous environment, that comprises
   directing to each of a plurality of regions at the surface of the body a pulse of laser radiation having sufficient energy density and sufficiently long wavelength to initiate in the adjacent gas a blast wave that impinges on the surface and provides an ultrasonic wave in the body, and
   detecting a portion of each such ultrasonic wave that has been affected by the body.

15. A method as in claim 14, wherein the detecting is done with a plurality of transducers, each maintained in a different location adjacent to, and spaced from, a surface of the body.

16. Apparatus for nondestructively testing a body of material having an electrically conductive surface in contact with a gaseous environment, that comprises
   means for directing to a region at the surface of the body a pulse of laser radiation having sufficient energy density and sufficiently long wavelength to initiate in the adjacent gas a blast wave that impinges on the surface and provides an ultrasonic wave in the body, and
   means for detecting a portion of the ultrasonic wave that has been affected by the body,
   the detecting means comprising an electromagnetic transducer that is resonant at substantially the fundamental frequency of the ultrasonic wave and is located adjacent to the conductive surface and spaced therefrom.

17. Apparatus as in claim 16, wherein the resonant frequency of the transducer is adjustable.

18. Apparatus as in claim 16, comprising also means for maintaining the transducer in its position at a substantially constant average spacing from the conductive surface during the testing.

19. Apparatus for nondestructively testing a body of material having a surface in contact with a gaseous environment, that comprises
   means for directing to each of a plurality of regions at the surface of the body a pulse of laser radiation having sufficient energy density and sufficiently long wavelength to initiate in the adjacent gas a blast wave that impinges on the surface and provides an ultrasonic wave in the body, and
   means for detecting a portion of each such ultrasonic wave that has been affected by the body,
   the detecting means comprising a plurality of transducers and means for maintaining each transducer in a different location adjacent to, and spaced from, a surface of the body.

* * * * *